US010130127B2

(12) United States Patent
Giulianotti et al.

(10) Patent No.: US 10,130,127 B2
(45) Date of Patent: Nov. 20, 2018

(54) SURGICAL SUIT

(71) Applicant: THE BOARD OF TRUSTEES OF THE UNIVERSITY OF ILLINOIS, Urbana, IL (US)

(72) Inventors: Pier Giulianotti, Urbana, IL (US); Arturo Vittori, Urbana, IL (US); Andreas Vogler, Urbana, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 545 days.

(21) Appl. No.: 14/897,640

(22) PCT Filed: Jun. 13, 2014

(86) PCT No.: PCT/US2014/042279
§ 371 (c)(1),
(2) Date: Dec. 10, 2015

(87) PCT Pub. No.: WO2014/201336
PCT Pub. Date: Dec. 18, 2014

(65) Prior Publication Data
US 2016/0128399 A1 May 12, 2016

Related U.S. Application Data

(60) Provisional application No. 61/834,506, filed on Jun. 13, 2013.

(51) Int. Cl.
A61B 5/00 (2006.01)
A41D 13/12 (2006.01)
(Continued)

(52) U.S. Cl.
CPC ......... A41D 13/1281 (2013.01); A41D 1/005 (2013.01); A41D 13/1263 (2013.01);
(Continued)

(58) Field of Classification Search
CPC ..... A61B 90/98; A41D 1/005; A41D 13/1263
(Continued)

(56) References Cited

U.S. PATENT DOCUMENTS 2,742,900 A 4/1956 Giorgio et al.
3,239,843 A 3/1966 Lobelle
(Continued)

FOREIGN PATENT DOCUMENTS

CN 203168090 9/2013
GB 828731 A 2/1960
(Continued)

OTHER PUBLICATIONS

International Search Report for PCT/US2014/042279 filed Jun. 13, 2014 on behalf of the Board of Trustees of The University of Illinois. dated Nov. 4, 2014.
(Continued)

Primary Examiner — Amanda Hulbert
Assistant Examiner — Philip C Edwards
(74) Attorney, Agent, or Firm — Steinfl + Bruno LLP

(57) ABSTRACT

A body surgical suit to be worn by surgery patients during surgical procedures, said body surgical suit being configured to encase the limbs and torso of a patient is described. The body surgical suit has one or more openings allowing to access one or more portions of the body of a patient wearing the body surgical suit, one or more sensors configured to monitor the patient's vital signs, a control monitor configured to control operation of the sensors, and selectively operatable contractive elements arranged in the legs and/or arms portions and configured to allow peristaltic movement of blood in the arms and legs of a patient wearing the body surgical suit.

21 Claims, 12 Drawing Sheets

(51) Int. Cl.
| | |
|---|---|
| *A61B 90/98* | (2016.01) |
| *A61B 5/0205* | (2006.01) |
| *A61H 9/00* | (2006.01) |
| *A61M 35/00* | (2006.01) |
| *A61N 1/04* | (2006.01) |
| *A41D 1/00* | (2018.01) |
| *A61B 5/021* | (2006.01) |
| *A61B 5/024* | (2006.01) |
| *A61B 5/0402* | (2006.01) |
| *A61B 5/11* | (2006.01) |

(52) U.S. Cl.
CPC .......... *A61B 5/02055* (2013.01); *A61B 90/98* (2016.02); *A61H 9/0057* (2013.01); *A61M 35/00* (2013.01); *A61N 1/0484* (2013.01); *A61B 5/021* (2013.01); *A61B 5/024* (2013.01); *A61B 5/0402* (2013.01); *A61B 5/1113* (2013.01)

(58) Field of Classification Search
USPC ........................................................ 600/513
See application file for complete search history.

(56) References Cited

U.S. PATENT DOCUMENTS

| | | | |
|---|---|---|---|
| 3,783,863 | A | 1/1974 | Kliever |
| 5,322,245 | A | 6/1994 | Bassick |
| 5,626,151 | A | 5/1997 | Linden |
| 5,975,081 | A | 11/1999 | Hood et al. |
| 6,047,203 | A | 4/2000 | Sackner et al. |
| 6,073,284 | A | 6/2000 | Borders |
| 6,112,333 | A | 9/2000 | Mazzei |
| 6,155,260 | A | 12/2000 | Lavin et al. |
| 6,245,028 | B1 | 6/2001 | Furst et al. |
| 6,401,278 | B1 | 6/2002 | Hayes et al. |
| 6,460,187 | B1 | 10/2002 | Siegel |
| 6,493,890 | B2 | 12/2002 | Smeed |
| 6,792,623 | B2 | 9/2004 | Luppi |
| 7,296,570 | B2 | 11/2007 | Hutchinson |
| 8,033,281 | B2 | 10/2011 | Kneale et al. |
| 2002/0138905 | A1 | 10/2002 | Bartlett et al. |
| 2003/0097060 | A1 | 5/2003 | Yanof et al. |
| 2004/0040064 | A1 | 3/2004 | Mah et al. |
| 2004/0267145 | A1 | 12/2004 | David et al. |
| 2006/0150335 | A1 | 7/2006 | Dankbaar et al. |
| 2009/0235928 | A1 | 9/2009 | Borsari |
| 2010/0031443 | A1 | 2/2010 | Georgiev et al. |
| 2010/0242150 | A1 | 9/2010 | Trouillot |
| 2011/0076771 | A1 | 3/2011 | Gabriele et al. |
| 2011/0289644 | A1 | 12/2011 | Beshlian |
| 2012/0136231 | A1 | 5/2012 | Markel |
| 2012/0146784 | A1 | 6/2012 | Hines et al. |
| 2012/0158074 | A1 | 6/2012 | Hall |
| 2012/0246795 | A1 | 10/2012 | Scheffler et al. |
| 2013/0085510 | A1 | 4/2013 | Stefanchik et al. |
| 2013/0178870 | A1 | 7/2013 | Schena |

FOREIGN PATENT DOCUMENTS

| | | |
|---|---|---|
| JP | 2006280534 | 10/2006 |
| JP | 2007175266 | 7/2007 |
| KR | 10-2011-0030038 A | 3/2011 |
| WO | 1992/18084 A1 | 10/1992 |
| WO | 1999/029235 A | 6/1999 |
| WO | 0000152 | 1/2000 |
| WO | 03/097145 | 11/2003 |
| WO | 2005/102084 A1 | 11/2005 |
| WO | 2007/128571 | 11/2007 |

OTHER PUBLICATIONS

Written Opinion for PCT/US2014/042279 filed Jun. 13, 2014 on behalf of the Board of Trustees of The University of Illinois. dated Nov. 4, 2014.
International Search Report for PCT/US2014/042286 filed Jun. 13, 2014 on behalf of the Board of Trustees of The University of Illinois. dated Nov. 4, 2014.
Written Opinion for PCT/US2014/042286 filed Jun. 13, 2014 on behalf of the Board of Trustees of The University of Illinois. dated Nov. 4, 2014.
International Preliminary Report on Patentability for PCT/US2014/042286 filed Jun. 13, 2014 on behalf of The Board of Trustees of the University of Illinois. dated Nov. 30, 2015.
International Search Report and Written Opinion for PCT/US2014/042277 filed Jun. 13, 2014 on behalf of The Board of Trustees of the University of Illinois. dated Nov. 7, 2014.
International Search Report and Written Opinion for PCT/US2014/042281 filed Jun. 13, 2014 on behalf of The Board of Trustees of the University of Illinois. dated Oct. 20, 2014.
International Preliminary Report on Patentability for PCT/US2014/042281 filed Jun. 13, 2014 on behalf of The Board of Trustees of the University of Illinois. dated Jun. 26, 2015.
International Preliminary Report on Patentability for PCT/2014/042279 filed Jun. 13, 2014 on behalf of The Board of Trustees of the University of Illinois. Dated Dec. 4, 2015.
International Preliminary Report on Patentability for PCT/2014/042277 filed Jun. 13, 2014 on behalf of The Board of Trustees of the University of Illinois. Dated Dec. 15, 2015.
Corrected International Preliminary Report on Patentability for International Application No. PCT/US2014/042279 filed Jun. 13, 2014 on behalf of The Board of Trustees of the University of Illinois. Dated Jan. 29, 2016.

SURGICAL SUIT

CROSS REFERENCE TO RELATED APPLICATIONS

The present application is the US national stage of International Patent Application PCT/US2014/042279 filed internationally on Jun. 13, 2014, which claims priority to U.S. Provisional Application No. 61/834,506 filed on Jun. 13, 2013 which is incorporated herein by reference in its entirety.

FIELD

The present disclosure generally relates to hospital clothing and in particular to a surgical suit to be worn by a hospital patient during surgery.

BACKGROUND

Patients in hospitals generally wear pajamas or gowns when they are in their rooms. Before and after surgery patients typically need to be connected to a number of devices such as e.g. drainage channels, catheters and the like, as well as to electronic monitoring devices requiring arrangement of sensors and routing of cables.

There are known hospital gowns configured to facilitate arrangement of such and similar devices. U.S. Pat. No. 6,460,187 and US 2010/024150 e.g. disclose hospital gowns comprising inside and outside pockets, as well as inside and outside hangers allowing to fit and accommodate various medical appliances such as e.g. telemetry transmitters with sensors attached to the patient, catheter units and drainage channels.

The international publication WO 2005/102084 describes a gown for hospital use provided with a removable element allowing to access the patient's body, in particular at the chest area, without being forced to undress the patient completely.

During surgery patients are instead almost naked and covered with sterile sheets that are typically arranged so as to define an access to a surgical site. A surgical site may be e.g. a portion of the abdomen in the case of laparoscopic surgery, the chest, a flank and the like.

Still during surgery monitoring sensors are typically placed on the patient's body in order to monitor his/her vital signs. This requires to arrange under the surgical sheets a number of cables that must be connected to respective monitoring devices located in an operating room. Such sensors may be e.g. blood pressure sensors, electrocardiology (ECG) electrodes, body temperature sensors and the like.

Surgical gowns allowing to protect privacy of the patients while not hindering surgery operations have been envisioned. Similarly to hospital gowns, also surgical gowns comprise pockets, hangers and openings allowing to fit and accommodate various medical appliances. The Chinese utility model CN 203168090 e.g. discloses a patient surgical gown which comprises a coat and trousers. The gown is provided with a number of openings and ports facilitating access to e.g. the abdominal cavity, chest drainage or intubation, endotracheal intubation and the like.

It is also known that during surgery a patient generally needs to be restrained to a surgical table so as to be kept in the correct position especially when the surgical table is inclined so as to exploit gravity as a means to move a patient's organs into a desired and more suitable position for the intervention. This is generally achieved by way of restraining means such as straps, fasteners and the like connected or connectable to the surgical table. The arrangement of cables and lines of monitoring devices must take into account the position of restraining means and possible maneuvers of the surgical table.

Hence, the preparation of patients for surgery is a time consuming and rather complex procedure.

Moreover, the patient must be protected against injuries connected with extreme, e.g. vertical, positions a surgical table may assume. Multiple anchoring points are generally preferred, because they allow to distribute contact pressures over a larger surface while decreasing the decubitus on focal points. However, the straps and fasteners presently employed in surgical tables do not always allow to achieve a proper pressure distribution of contact pressures.

Emergency devices such as e.g. defibrillators must also be present in an operating room. In order to use these emergency devices surgical sheets and/or patient monitoring devices must be partially or completely removed. Since emergency procedures must be carried out very quickly, preparation and arrangement of sterile sheets and monitoring devices have to take into account also emergency situations, which makes preparation procedures even more complex and time consuming.

Hence, there is an increased need for improving patient handling and monitoring during surgery.

SUMMARY

The present disclosure is a surgical suit to be worn by surgery patients during surgical procedures.

The surgical suit is made of materials having antimicrobial properties so as to encase the patient's body in a sterile environment and comprises at least one opening for performing a surgical procedure and one or more openings for infusions.

The surgical suit further comprises one or more sensors for monitoring the patient's vital signs such as e.g. ECG measuring sensors, blood pressure and heart beat sensors. A control monitor of the surgical suit is configured to control operation of such sensors.

The surgical suit may further comprise a massaging system in turn comprising selectively operatable contractive elements e.g. of a pneumatic type arranged in the legs and/or arms portions. The massaging system is particularly configured to allow peristaltic movement of blood in the arms and/or legs of the patient wearing the surgical suit.

The surgical suit may further comprise emergency devices such as defibrillator pads, as well as muscle-stimulating electric activators helping a patient to quickly recover after surgery.

Monitoring sensors and contractive elements, as well as defibrillator pads and muscle-stimulating electric activators are built-in components of the surgical suit. The electrical wires of these devices are embedded in the fabric structure of the surgical suit and so arranged to have a single electric output allowing connection of all the built-in components to the respective devices arranged in an operation room.

The surgical suit may also comprise an electronic unit configured for wireless transmission of the data acquired from the patient to remote data processing systems, as well as transmission of inputs from remote control systems in order to drive electronic devices of the surgical suit such as defibrillator pads and muscle-stimulating electric activators.

The surgical suit may further comprise built-in patient information means allowing medical staff to automatically have information about the patient wearing the surgical suit. Patient information may in particular comprise data about the patient's disease and the type of surgical intervention to be carried out, so that the risk of mistakes during surgery is minimized. Such means may e.g. comprise radio-frequency identification (RFID) tags. Electric units provided with a display may be used as well.

According to an embodiment of the present disclosure, the surgical suit is made up of individual composable portions that may be assembled together e.g. by way of zippers, buttons, hook and loop strips and the like. The built-in components are associated with one or more single composable portions, so that the surgical suit may be configured based on specific patient's needs. The sensors may advantageously be of a wireless type powered by way of batteries embedded in their respective individual portions, so that electrical connections between adjacent modules is not necessary.

According to a further embodiment of the present disclosure, the surgical suit may also include a vacuum system comprising sucking channels connected to respective suctions cups arranged on portions of the surgical suit intended to face a surgical table, more generally a patient supporting surface. The sucking channels may advantageously be connected to a common suction port arranged on a portion of the surgical suit and configured to be attached to a vacuum system provided in an operation room. The vacuum system allows to restrain a patient wearing the surgical suit to a surgical table without resorting to traditional straps and fasteners.

Thanks to these features the surgical suit may advantageously be used not only during surgery, but also during procedures preceding it like e.g. induction of anesthesia and following it, like wake-up after anesthesia, as well as during the whole hospitalization period.

DETAILED DESCRIPTION

Figure 1:
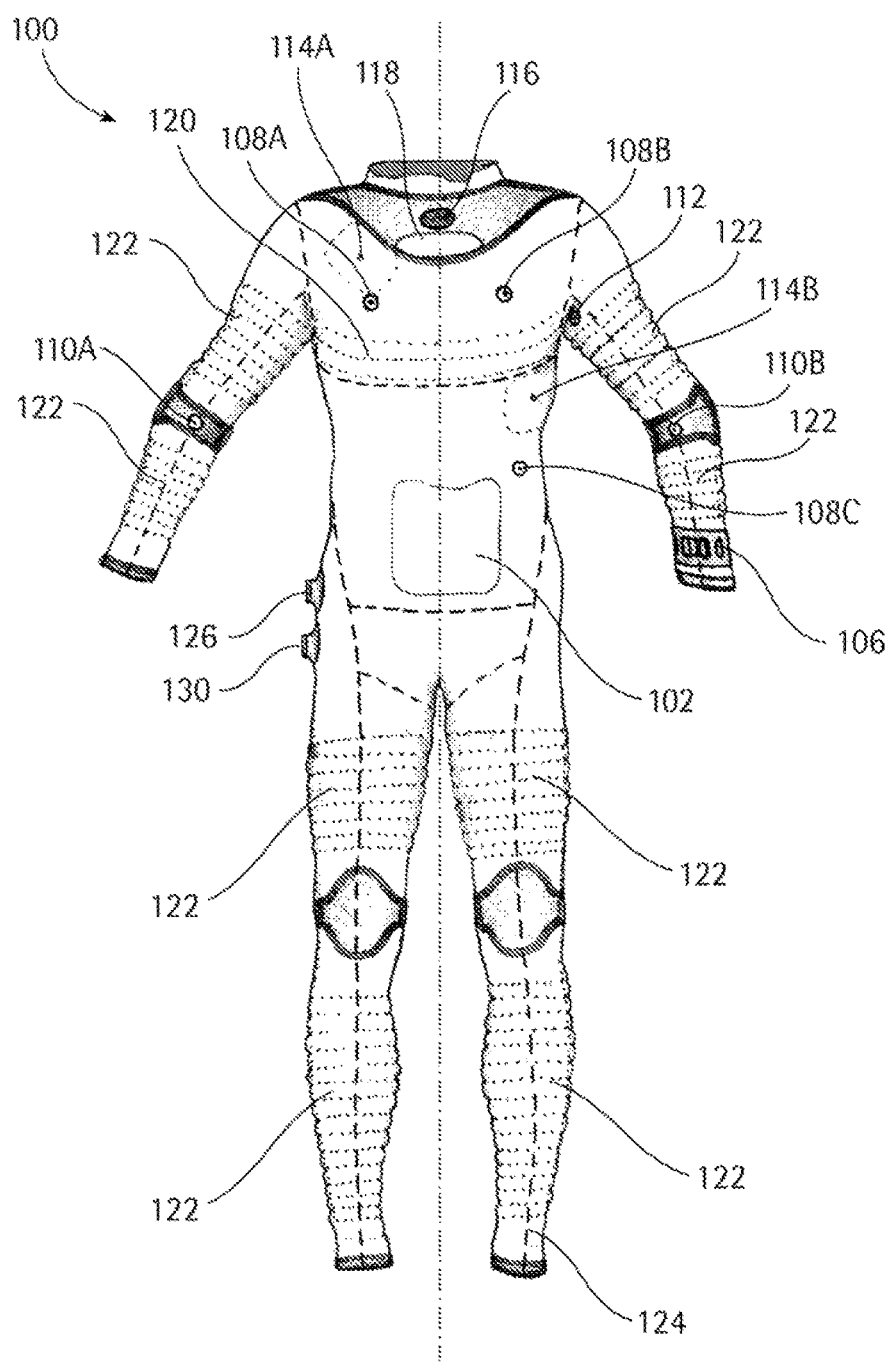
FIGS. 1, 2 and 3 respectively show a front, a rear and a back view of a surgical suit according to an embodiment of the present disclosure.
Figure 2:
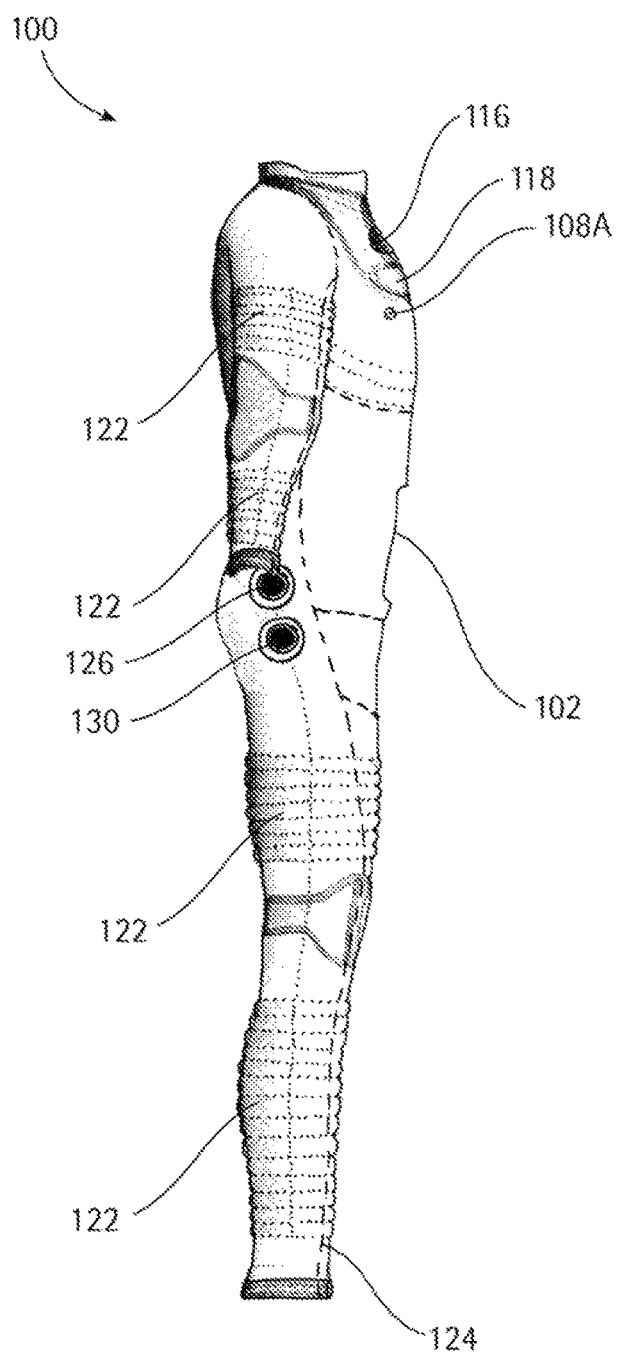
Figure 3:
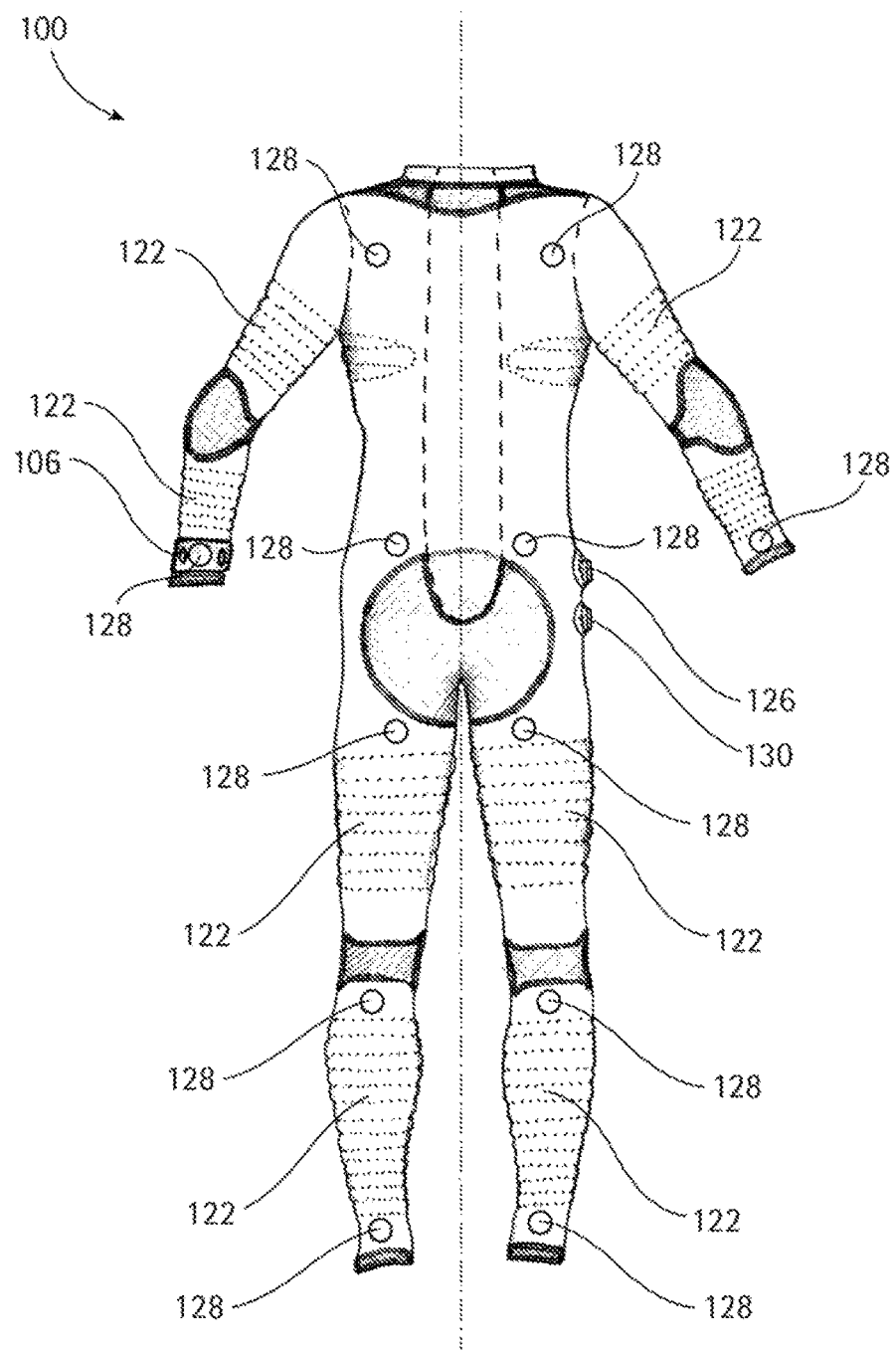

FIGS. 1, 2 and 3 respectively show a front, a rear and a back view of a surgical suit according to an embodiment of the present disclosure to be worn by surgery patients during surgical procedures. The surgical suit is generally indicated by reference number 100.

The surgical suit 100 encases the limbs and torso of a patient thus substantially fully isolating the body from the external environment. It is known in fact that a high risk of infection of patients during surgery stems from their own body hair, which are exposed to the external environment although covered by surgical sterile sheets.

The surgical suit 100 comprises one or more openings formed at the predetermined place of a surgical intervention. In the illustrated embodiment the surgical suit e.g. comprises a single window-shaped rectangular opening 102 formed in the portion intended to cover the abdomen of a patient, which may be used for laparoscopic surgery. The openings may already be present in the surgical suit 100 or may be obtained by selectively removing portions thereof along suitable perforations lines.

Further openings allowing infusion may advantageously be formed in the surgical suit 100. Infusion openings 110A, 110B may e.g. be formed in the arm portions of the surgical suit 100. Further openings may advantageously be provided at genital and perianal areas for catheterization or other procedures.

The surgical suit 100 is made of a material having antimicrobial properties so as to protect surgery patients against infections. The risk of infection is thus minimized thanks to the provision of a surgical suit isolating the body from the external environment, as well as to the choice of a textile preventing growth of bacteria. In addition to this, preferred is the use of breathable antimicrobial fabric materials, which allow air circulation and thus contribute to minimize growth of bacteria.

Suitable materials for this purpose are e.g. textiles comprising antimicrobial silver finish, such as the fabrics sold under the trademark TREVIRA Bioactive.

The surgical suit 100 comprises one or more sensors for monitoring the patient's vital signs. The sensors are built-in components of the surgical suit 100 and may e.g. comprise ECG sensors 108A, 108B, 108C located in the chest portion, body temperature sensors 112 e.g. located at an armpit portion, patient position sensors 116 e.g. located at a neck portion.

The surgical suit 100 may also comprise further sensors adapted to monitor pulse and oxygen in blood, blood pressure, heart beat and airflow during intubation. Electromyography and Galvan skin response sensors may also be integrated in the surgical suit 100 according to an embodiment of the present disclosure.

The surgical suit 100 may further advantageously comprise emergency devices such as defibrillator pads 114A, 114B located at the portions intended to contact the right side of the patient's sternum just below the clavicle and the left anterior axillary line between the fifth and the sixth ribs.

Muscle-stimulating electric activators helping a patient to quickly recover after surgery may also be integrated in the surgical suit 100.

Operation of the sensors and devices may be displayed and possibly controlled by way of a control monitor 118 of the surgical suit e.g. arranged in the chest portion.

The electrical wires and cables of these sensors and devices are embedded in the dress fabric structure thus avoiding their direct contact with the patient's skin and may advantageously be arranged so as to have a single electric input/output member 126 allowing connection of all the built-in components to the respective devices arranged in an operation room.

As shown in the drawings, the electric input/output member 126 may e.g. be located on a side portion of the surgical suit 100 at the patient's left or right hip so as not to interfere with the surgical tools during an intervention.

Additionally or alternatively, the surgical suit may comprise an electronic unit with a microprocessor operatively coupled to the sensors and devices and configured for wireless transmission of the data acquired from the patient to remote processing systems, as well as transmission from remote control systems of inputs for driving electronic such as defibrillator pads and muscle-stimulating electric activators.

The electronic unit is indicated in the drawings by reference numeral 106 and may be arranged e.g. at a wrist portion of the surgical suit 100.

The surgical suit 100 may advantageously further comprise built-in patient identification and information means allowing medical staff to automatically identify and have information about the patient wearing the surgical suit. The medical staff may thus be prompted with information about the health condition of a patient, the surgical intervention to be carried out and the like, thus allowing to minimize the risk of mistakes especially during surgery.

Such means may e.g. comprise RFID tags or may be directly integrated in the control monitor 118.

In order to ensure a proper contact between monitoring and emergency devices and the patient's body, the surgical suit 100 is preferably made of a fabric having elastic properties, i.e. comprising elastic fibers, so that a skin-tight configuration may be obtained.

According to an embodiment of the present disclosure, the surgical suit 100 is made up of individual composable portions that may be assembled together e.g. by way of fastening means such as e.g. zippers, buttons, hook and loop strips and the like in order to form a complete surgical suit.

The built-in components of the surgical suit 100, i.e. the above-described sensors and electronic devices, are associated with one or more single composable portions, so that the surgical suit may advantageously have a modular structure to be configured based on specific patient's needs.

This solution is advantageous also because it allows not to cover portions of a patient's body wherein possible injuries such as e.g. deep wounds, skin burns and the like, are present and need to be treated.

The modular portions intended to cover parts of the body after surgery, e.g. abdomen portion 102, may advantageously be made of artificial skin materials, such as materials made of biopolymers, promoting growth of natural tissues through controlled dispensing of medical treatments. A suitable material for this purpose is a polyester-urethane based material sold under the trademark DegraPol®. In this case also body portions wherein injuries are present may be covered by the surgical dress according to an embodiment of the present disclosure and treated by using the dress structure itself.

According to this embodiment of the present disclosure, the sensors associated with single portions of the surgical suit 100 are preferably wireless sensors configured to exchange data and information with a remote control unit, directly or e.g. through the electronic unit 106.

The wireless sensors of each portion of the surgical suit 100 are preferably powered by way of batteries embedded in the same portion. This solution is advantageous because the single portions of the surgical suit 100 are independent working modules that need no electrical connections among each other, nor to a common electric input/output member 126 as described in the previous embodiments of the present disclosure.

In FIGS. 1 to 3 the surgical suit 100 is shown in an assembled configuration and its individual composable portions are marked by way of dashed lines 124 representing fastening lines. Along these lines may zippers may e.g. be provided. Referring to the front view of FIG. 1, a chest portion may be seen wherein ECG sensors 108A, 108B, a first defibrillator pad 114A, position sensor 116 and control monitor 118 are embedded or fitted.

The chest portion is laterally connected to left and right arm portions. The left arm portion comprises an armpit temperature sensor 112 and the electronic unit 106.

The chest portion is also connected to an abdomen portion wherein the opening 102 allowing to access the abdominal cavity of a patient is formed. The abdomen portion comprises a second defibrillator pad 114B and a further ECG sensor 108C.

Below the abdomen portion an inguinal portion is connected, which is in turn connected to left and right leg portions.

Now referring to FIG. 3, it may be seen that on the back of the surgical suit 100 the left and right leg portions extend up to the neck portion forming a back portion. Such back portion may comprise a removable central portion extending from the neck to the bottom portion allowing to ease wearing of the surgical suit. The back portion may also advantageously comprise a further removable portion intended to cover the patient's bottom. This portion forms a single member with the inguinal portion in order to allow to access the inguinal area of a patient to fit urinary catheters or to put diapers without undressing the patient.

Figure 4:
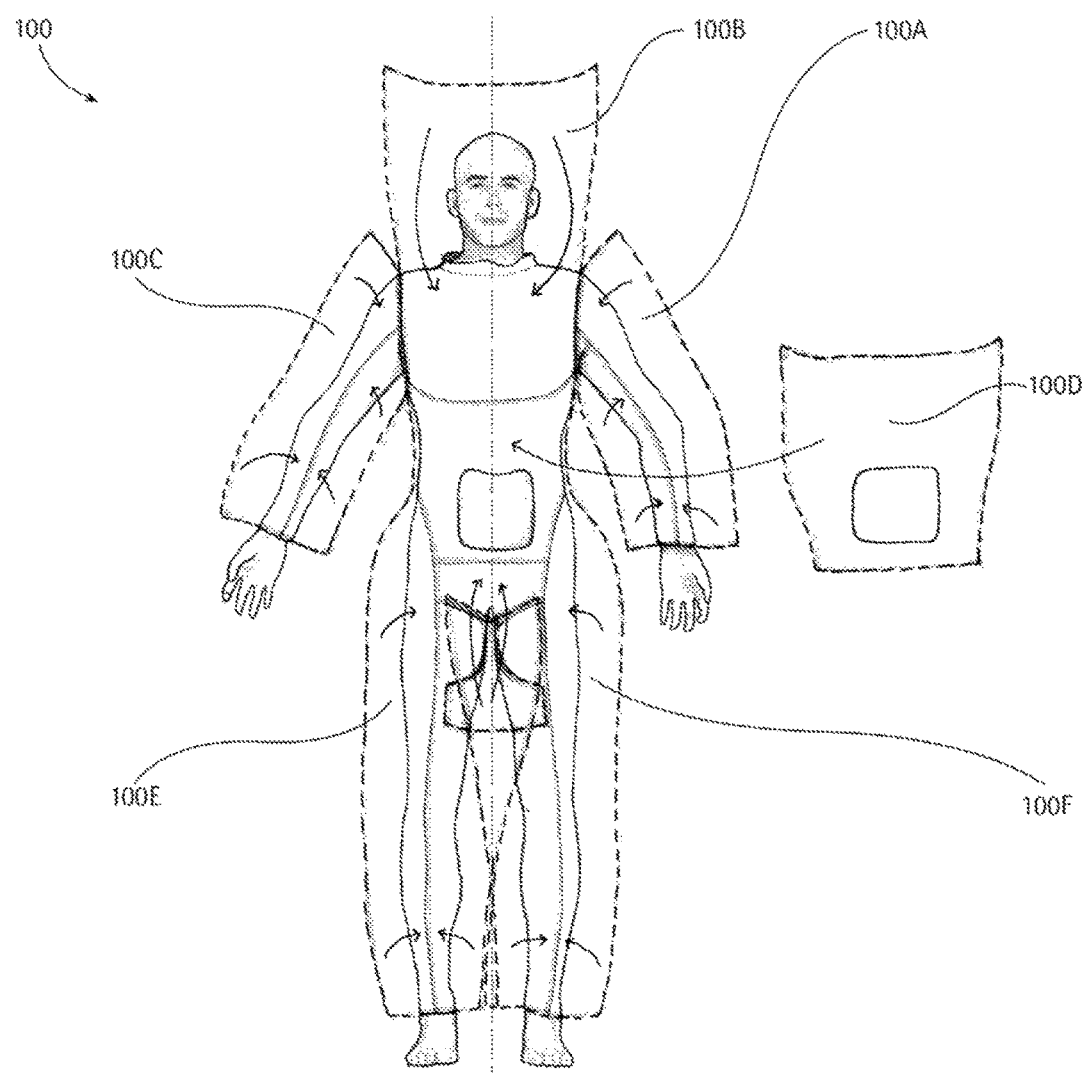
FIGS. 4 and 5 show subsequent assembly steps of the surgical suit according to an embodiment of the present disclosure on a patient.
Figure 5:
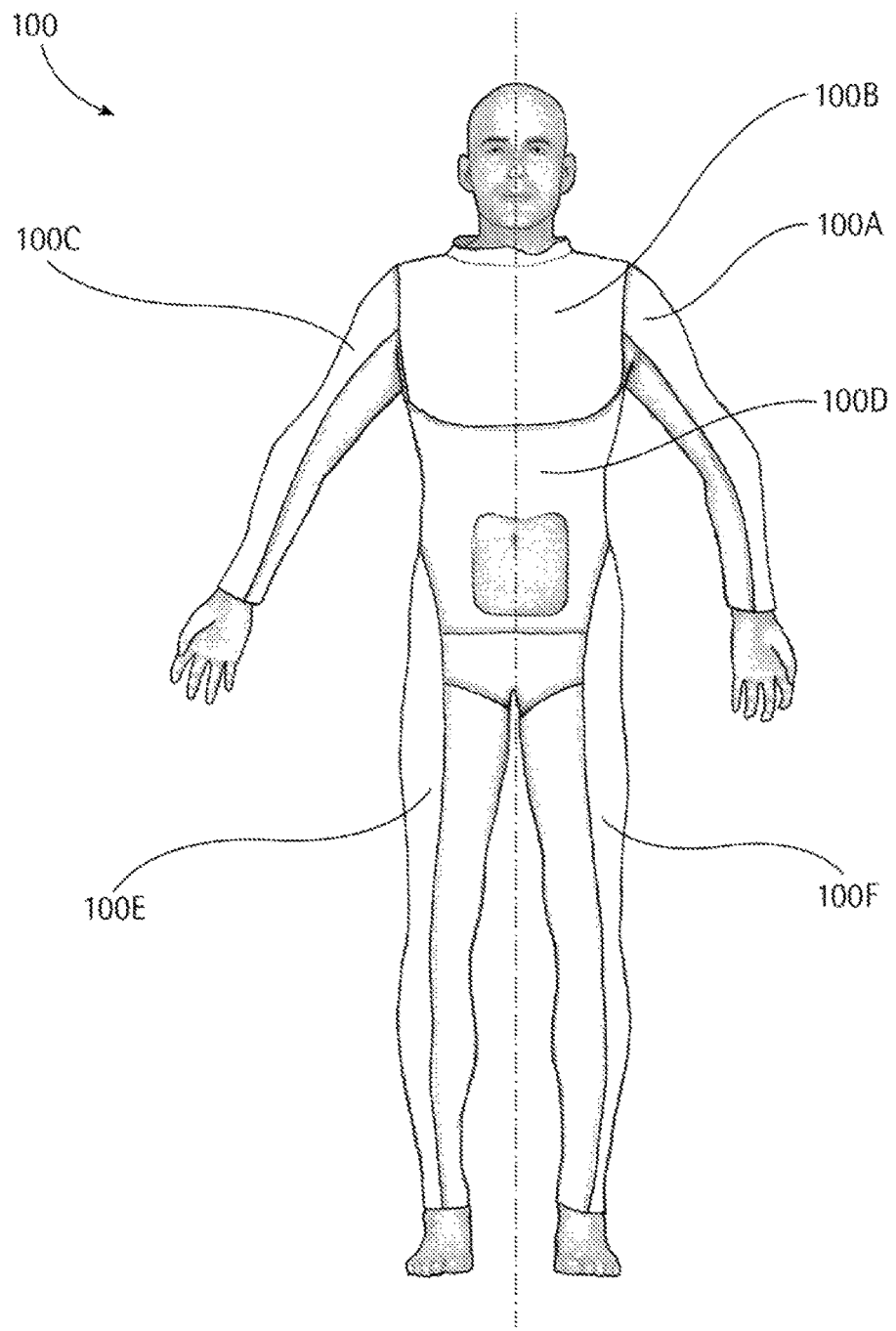

FIGS. 4 and 5 schematically show assembly operations of the individual composable portions 100A to 100F of the surgical suit 100 on a patient.

According to an embodiment of the present disclosure, the surgical suit 100 may further integrate selectively operatable contractive elements, e.g. of a pneumatic type, arranged in the legs and/or arms portions and particularly configured to allow peristaltic movement of blood in the arms and/or legs of the patient wearing the surgical suit. Inflation and deflation of the contractive elements can be automatically controlled by a computer using suitable algorithms.

Still referring to FIGS. 1 to 3, in the illustrated embodiment contractive elements are associated with both arms and leg portions of the surgical suit 100. The contractive elements comprise a plurality of bladders 122 made of an expandable elastic material such as e.g. butyl rubber surrounding arms and leg portions in a ring-like manner. The bladders 122 are arranged parallel to one another and sandwiched between two layers of fabric in the longitudinal direction of arms and legs and are individually fed by a fluid medium under pressure such as e.g. air by way of channels embedded or formed in the fabric structure of the surgical suit 100.

The flow of the fluid medium in each bladder is automatically controlled by way of a respective bladder valve, e.g. a solenoid valve, operably connected to a remote control unit. The fluid medium may be supplied to the various channels through a single common port e.g. integrated in the electric input/output member 126.

Figure 6:
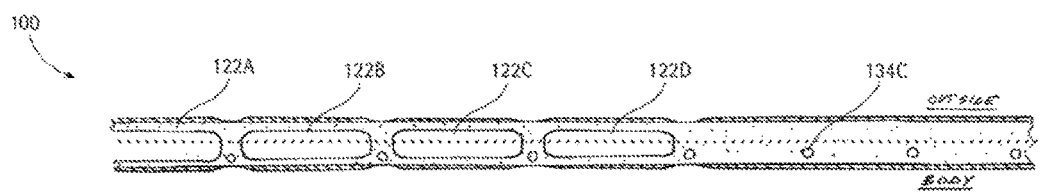
FIGS. 6, 7 and 8A are partial cross sectional views of a portion of the surgical suit wherein contractive elements in the form of bladders are arranged.
Figure 7:
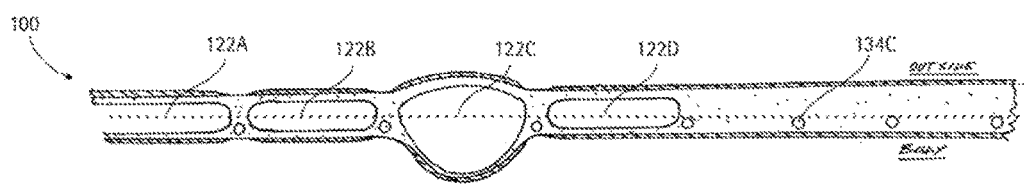

FIGS. 6 and 7 show a cross section of a portion of the surgical suit 100 wherein bladders 122A, 112B, 112C and 112D may be seen. In FIG. 6, all the bladders 122A to 112D are deflated, whereas in FIG. 7 one of them, e.g. bladder 112C, is inflated by the fluid medium thus allowing to compress the patient's body locally.

Figure 8A:
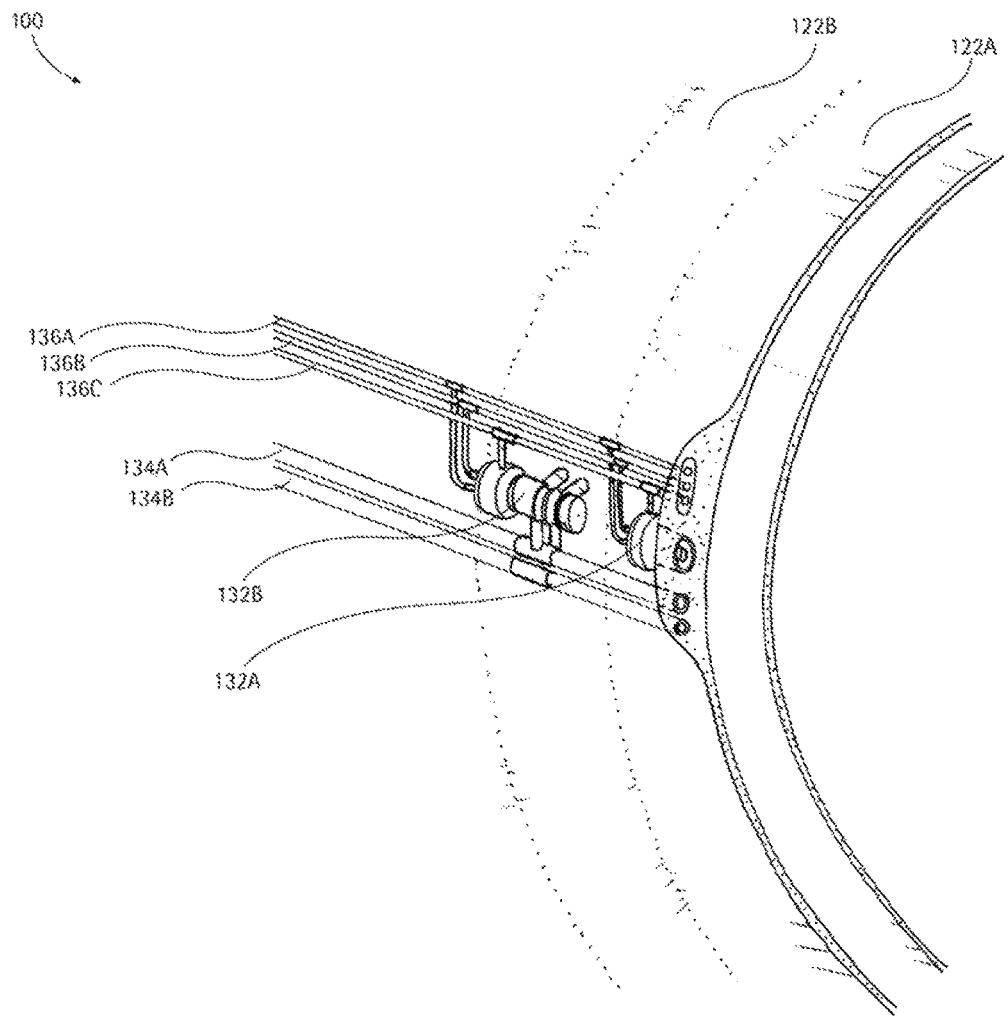

FIG. 8A is a perspective view schematically showing bladders 122A, 112B, their respective valves 132A, 132B and related fluid medium supply channels 134A, 134B serving as inflation and deflation lines, respectively. The valves 132A, 132B are connected to power supply lines 136A, 136B and to a data line 136C.

Figure 8B:
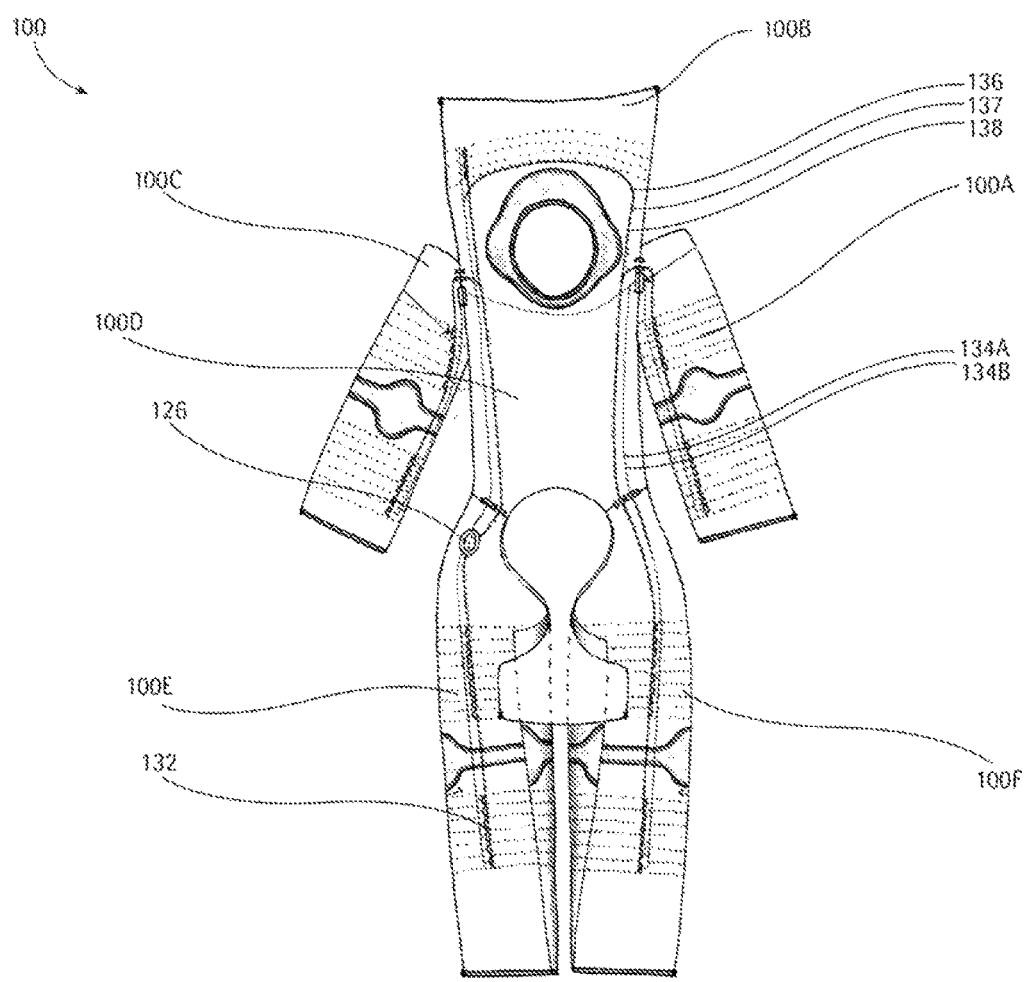
FIG. 8B is a front view of the surgical suit in an open and spread out configuration showing locations of the contractive elements.

FIG. 8B is a front view of the surgical suit 100 in an open and spread out configuration showing the locations of the contractive elements, their respective valves, power supply and data lines.

Provision of the contractive elements is also useful for counteracting blood shift when a patient is inclined during a surgical procedure in order to exploit gravity as a means to move internal organs to ease access to the body portion to be operated.

The fluid medium used to operate the bladders may also advantageously be used as a means for temperature regulation. To this aim the source of the fluid medium may comprise a temperature control system configured to adjust the temperature of the fluid medium to be supplied to the contractive elements.

This feature according to an embodiment of the present disclosure is particularly advantageous e.g. to counteract hypothermia, which typically occurs as a consequence of long surgical procedures.

Hence, not only body temperature may be monitored, but also suitably adjusted, i.e. decreased or increased, in order to maintain homeostasis.

According to an alternative embodiment of the present disclosure, temperature regulation may be achieved independently by way of additional pipelines integrated in the surgical suit, wherein a fluid medium other than the fluid medium used to operate the contractive elements is employed. Hence, in this case the surgical suit includes a temperature regulation system.

Figure 8C:
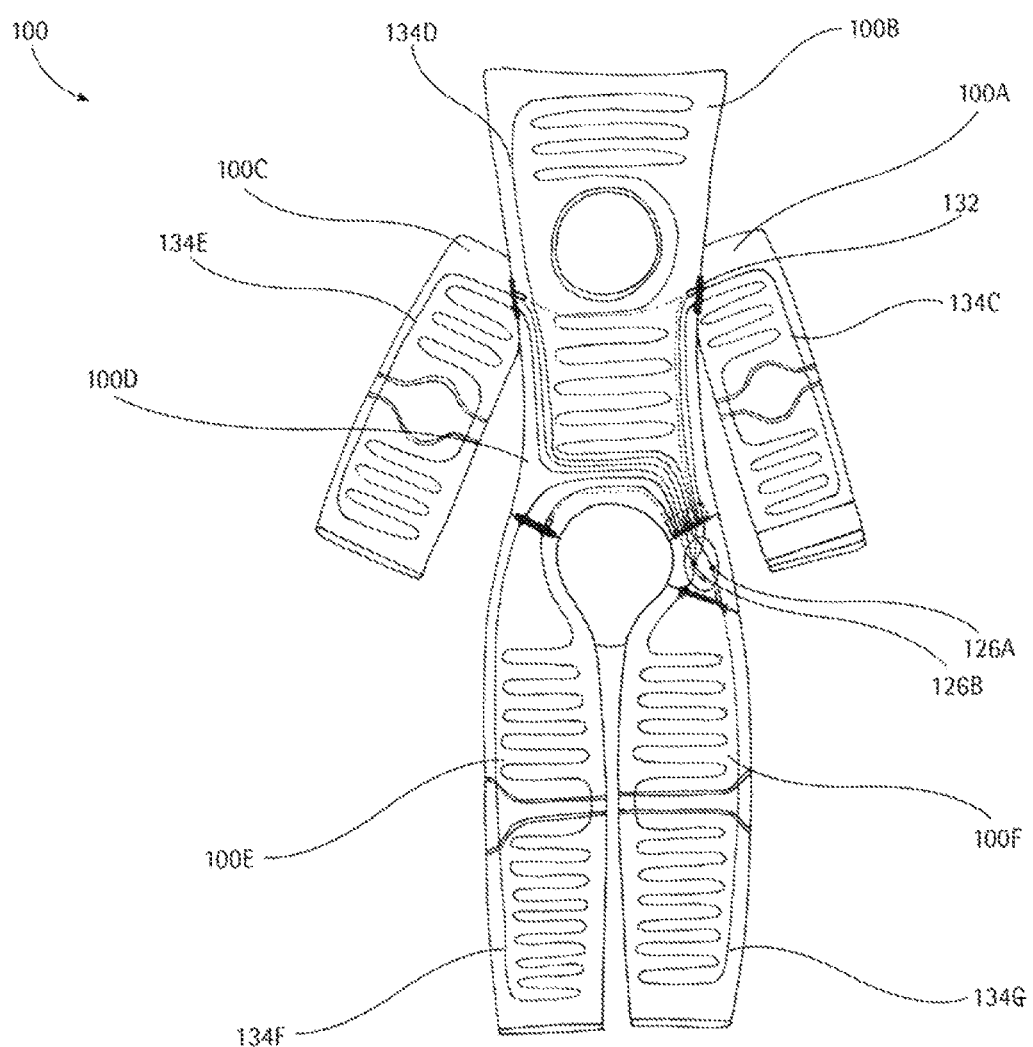
FIG. 8C shows an exemplary layout of a pipeline of a temperature regulation system of the surgical suit.

FIG. 8C shows an exemplary layout of pipelines of the temperature regulation system. Each pipeline is configured as a closed path starting and ending at ports configured to supply and receive the fluid medium. Such ports are indicated by reference numbers 126A and 126B and are preferably integrated in the electric input/output member 126. As shown in the figure, starting from port 126A a first pipeline 134C runs through the left arm portion 100A. A second pipeline 134D runs through the chest and back portion 100B. A third pipeline 134E runs through the right arm portion 100C, a forth and a fifth pipelines 134F and 134G run through leg portions 100E and 100F, respectively.

According to a further embodiment of the present disclosure, the surgical suit 100 may include a vacuum system comprising a plurality of sucking channels connected to suctions cups arranged on portions of the surgical suit intended to face a surgical table and more generally a patient supporting surface.

Figure 9:
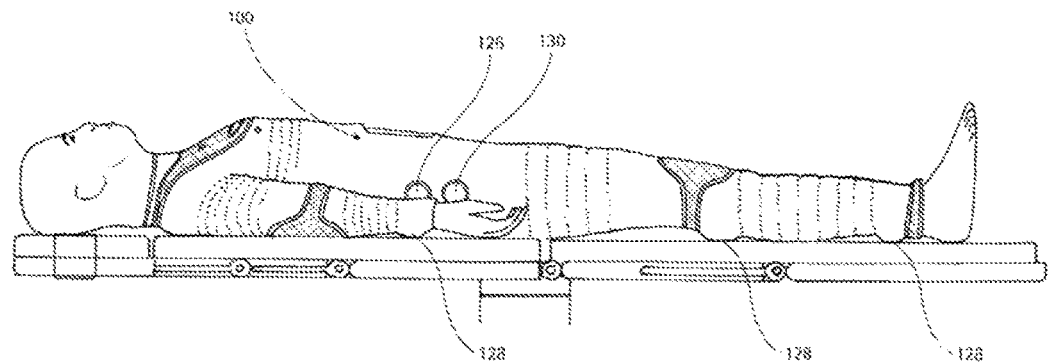
FIG. 9 shows a patient wearing a surgical suit according to an embodiment of the present disclosure and laying flat on a supporting surface, wherein the surgical suit comprises a vacuum system allowing to restrain the patient on a surgical table without resorting to traditional straps and fasteners.

The vacuum system allows to restrain a patient wearing the surgical suit 100 to a surgical table without resorting to traditional straps and fasteners and shown in FIG. 9. The sucking channels may advantageously be connected to a common single port 130 arranged on a portion of the surgical suit and configured to be attached to a vacuum system provided in an operation room through a suitable suction duct. In the illustrated embodiment the port 130 is shown arranged e.g. on a right side portion of the surgical suit 100 proximate to the electric input/output member 126.

Figure 10A:
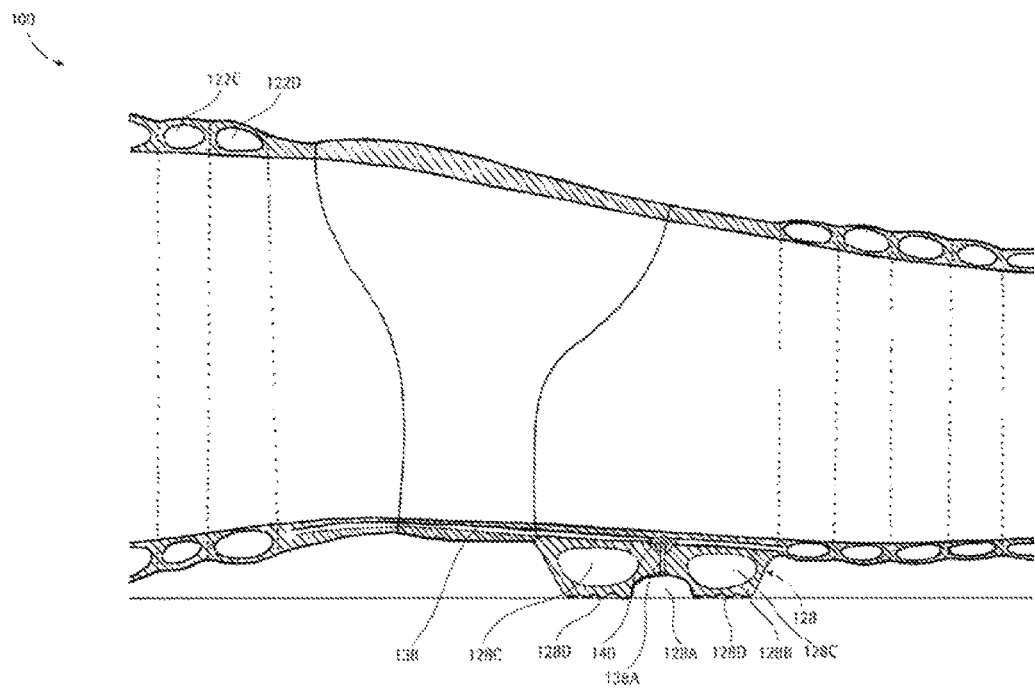
FIG. 10A is a detailed view showing a cross section of a knee portion of the surgical suit, wherein a sucking channel and a suction cup of a vacuum system of the surgical suit are arranged.

As shown in FIG. 10A suction ducts 138 of the sucking system are formed in a polymeric material layer, e.g. silicone, e.g. by way of a vacuum forming process and sandwiched between two fabric layers. Suction cups 128, e.g. made of the same polymeric material forming the layer wherein the suction ducts 138 are formed, are connected to the suction ducts 138 and so configured to protrude outwards relative to the surgical suit 100. Hence, the suction ducts 138 and the suction cups 128 form part of the surgical suit 100 and do not directly contact the patient's body.

This arrangement of the suction cups 128 allows to exert a sucking action on a surface supporting a patient wearing the surgical suit 100, e.g. a surgical table, thus restraining the patient to said surface.

Still referring to FIG. 10A, the flow rate of the air sucked by the vacuum system may be controlled by way of e.g. solenoid valves 140 arranged in each suction cup 128.

The suction cups 128 may have a conical shape comprising a recess 128A formed at their free ends and defining a rim 128B intended to contact a patient supporting surface. Branches 138A of the channels 138 terminate at the recess 128A.

The suctions cups 128 may also comprises hollow portions 128C and ripples 128D formed on the rim 128B allowing make them more deformable to improve effectiveness of their sucking action on the patient supporting surface.

Still referring to FIG. 3, a suitable arrangement of the suction cups 128 on the back side of the surgical suit 100 is shown. As it may be seen, the suction cups 128 are arranged at wrist and shoulder portions, at the back and bottom portions, as well as on the leg portions.

Figure 10B:
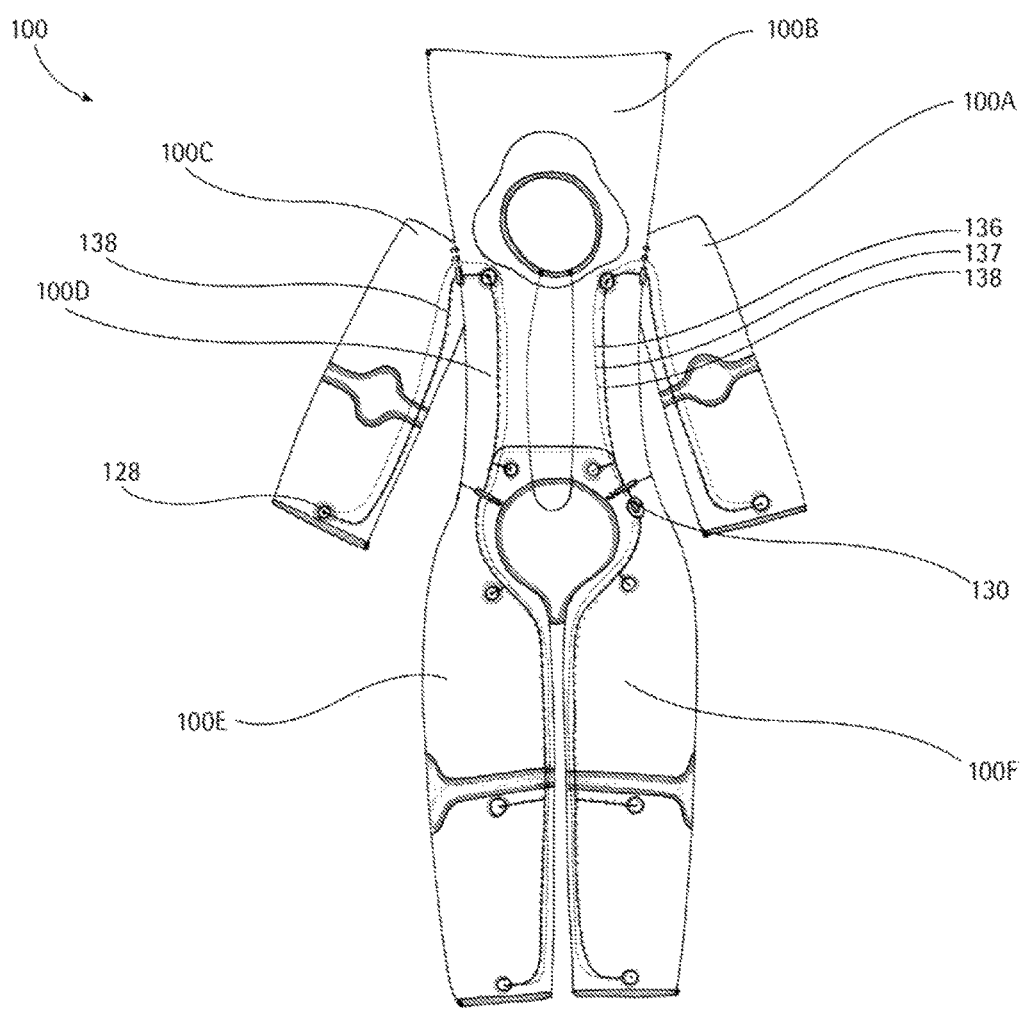
FIG. 10B is a front view of the surgical suit in an open and spread out configuration showing the locations of the suction cups and of the suction ducts of the vacuum system.

FIG. 10B is a front view of the surgical suit 100 in an open and spread out configuration showing the locations of the suction cups 128 and of the suction ducts 138. According to the position of the supporting surface relative to the ground, and hence of the patient, a different restraining force may be required to keep the patient in the correct position.

When the patient lies flat on the supporting surface in fact, the latter bears the full weight of the patient thus requiring a minimum restraining force in order to prevent the patient from being accidentally moved e.g. during surgery. When e.g. during surgery the surgical table needs to be moved relative to the ground so as to exploit gravity as a means to shift the internal organs of the patient in order to ease access of surgical tools and facilitate their maneuvering, a higher restraining force is required to prevent the patient from moving relative to the surgical table or even falling therefrom.

The restraining force may be automatically set by way of a control system controlling operation of the vacuum system based on input signals provided by the patient position sensor 116 of the surgical suit 100.

Thanks to the provision of a sucking system, the patient may be firmly held on a supporting surface in any position relative to the ground. The sucking system also allows to protect the patient against injuries connected with extreme, e.g. vertical, positions the supporting surface, e.g. a surgical table may assume. An arrangement of the suctions cups such as the one shown in FIG. 10B allows to have multiple anchoring points not only at legs and arms like traditional straps and fasteners, but also on the back of the patient, thus allowing to distribute contact pressures over a large surface area while minimizing risks of decubitus at focal points.

When the surgical suit comprises individual composable portions a need exist to connect the power supply and data lines, as well as the fluid medium channels of the massaging system, the suction ducts of the vacuum system arranged in adjacent portions of the surgical suit and the possible pipelines of the temperature regulation system.

Figure 11:
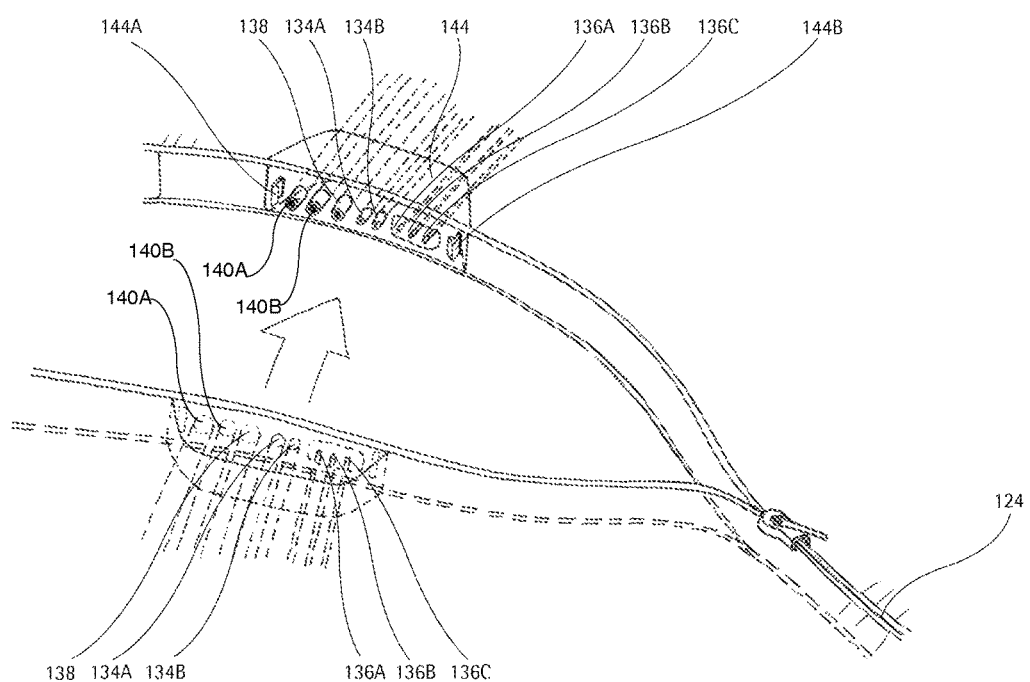
FIG. 11 is a detailed view schematically showing coupling means allowing to connect along fastening lines adjacent portions of the surgical suit wherein electric and hydraulic lines are arranged.

As shown in FIG. 11, to this aim coupling means are provided along fastening lines 124. As it may be seen, along the edge of one of the two adjacent portions a number of male connectors protrude, whereas on the edge of the other adjacent portion female connectors configured to receive the male connectors are arranged. Such connectors include electrical connectors respectively associated to the power supply lines 136A, 136B and to the data line 136C of the solenoid valves 132. The connectors also include hydraulic connectors for the channels 134A, 134B supplying a fluid medium to the contractive elements of the massaging system, as well as hydraulic connectors for the suction ducts 138 of the vacuum system and a hydraulic connector of the pipeline 134C.

Further connectors 140A, 140B may be provided for the pipelines of the temperature regulation system.

The coupling means may also advantageously comprise snap fit mechanical connectors 144A, 144B allowing to achieve a stable connection between the above mentioned electrical and hydraulic connectors.

It is understood that the foregoing detailed description and accompanying examples are merely illustrative and are not to be taken as limitations of the scope of an embodiment of the present disclosure, which is defined solely by the appended claims and their equivalents. Various changes and modifications to the disclosed embodiments will be apparent to those skilled in the art.

The invention claimed is:

1. A surgical suit to be worn by surgery patients during surgical procedures, said surgical suit being configured to encase the limbs and torso of a patient and comprising:
one or more openings allowing to access one or more portions of the body of a patient wearing the surgical suit;
one or more sensors configured to monitor the patient's vital signs;
a control monitor configured to control operation of said sensors; and
selectively operable contractive elements arranged in the legs and/or arms portions and configured to allow peristaltic movement of blood in the arms and legs of a patient wearing the surgical suit,
wherein:
said sensors are built-in components of the surgical suit, and
electrical wires and cables of the sensors and said control monitor are embedded in the suit fabric structure and arranged so as to have a single electric output allowing connection of all the built-in components to the respective devices arranged in an operation room
and wherein:
said surgical suit further includes a vacuum system comprising a plurality of sucking ducts ending with suctions cups, said suction cups being arranged on portions of the surgical suit intended to face a patient supporting surface.

2. The surgical suit of claim 1, wherein the sucking ducts are connected to a single common sucking port arranged on a portion of the surgical suit and configured to be attached to a vacuum system provided in an operation room.

3. The surgical suit of claim 1, wherein the ducts of the sucking system are formed in a polymeric material layer sandwiched between two fabric layers and wherein suction cups are embedded or simply connected to the end of the ducts and so configured to protrude outwards relative to the surgical suit.

4. The surgical suit of claim 1, wherein the suction cups are arranged on a back side of the surgical suit at wrist and shoulder portions, at back and bottom portions, as well as at leg portions.

5. The surgical suit of claim 1, wherein each suction cup comprises means configured to allow to adjust the flow rate of the air sucked by a vacuum system provided in an operation room to which the surgical suit is attached.

6. The surgical suit of claim 1, wherein said sensors comprise electrocardiology (ECG) sensors, body temperature sensors, patient position sensors, as well as blood pressure and heart beat sensors.

7. The surgical suit of claim 1, further comprising defibrillator pads, wherein said defibrillator pads are arranged at the portions configured to contact the right side of the patient's sternum just below the clavicle and the left anterior axillary line between the fifth and the sixth ribs and wherein the defibrillator pads are operably connected to the control monitor.

8. The surgical suit of claim 1, further comprising an electronic unit with a microprocessor operatively connected to the sensors and devices and configured for wireless transmission of data to and from said sensors and devices.

9. The surgical suit of claim 1, further comprising built-in patient identification and information means configured to automatically identify a patient wearing the surgical suit and to provide information about him/her.

10. The surgical suit of claim 9, wherein patient identification and information means comprise radio-frequency identification (RFID) tags.

11. The surgical suit of claim 9, wherein patient identification and information means are integrated in the control monitor of the surgical suit.

12. The surgical suit of claim 1, wherein said surgical suit is made of a material having antimicrobial properties.

13. The surgical suit of claim 12, wherein said antimicrobial material is a breathable fabric material.

14. The surgical suit of claim 12, wherein said breathable fabric material comprises elastic fibers.

15. The surgical suit of claim 1, wherein said surgical suit is made up of individual composable portions that may be assembled together by way of fastening means.

16. The surgical suit of claim 15, wherein said fastening means comprise zippers, buttons and hook and loop strips.

17. The surgical suit of claim 15, wherein composable portions intended to cover parts of the body of a patient that have been subjected to surgery are made of artificial skin materials.

18. The surgical dress of claim 17, wherein said artificial skin materials are made of biopolymers promoting growth of natural tissues through controlled dispensing of medical treatments.

19. The surgical suit of claim 1, wherein said contractive elements comprise a plurality of bladders made of an expandable elastic material and wherein said bladders are arranged parallel to one another in the longitudinal direction of arms and/or legs portions.

20. The surgical suit of claim 19, wherein the flow of the fluid medium in each bladder is automatically controlled by way of a respective bladder valve operably connected to a remote control unit.

21. The surgical suit of claim 19, wherein the bladders arranged in each arm and/or leg portion of the surgical suit are connected in parallel to respective supply channels extending along them.

* * * * *